United States Patent [19]

Yoneda

[11] Patent Number: 6,070,986
[45] Date of Patent: Jun. 6, 2000

[54] METHOD OF MANUFACTURING A LIGHTING UNIT FOR INSPECTING A SURFACE

[75] Inventor: Kenji Yoneda, Kyoto, Japan

[73] Assignee: CCS Co., Ltd., Japan

[21] Appl. No.: 08/878,199

[22] Filed: Jun. 18, 1997

[30] Foreign Application Priority Data

Jul. 8, 1996 [JP] Japan .................................. 8-178034

[51] Int. Cl.[7] .................................................. A61G 13/00
[52] U.S. Cl. ............................................. 362/33; 362/33
[58] Field of Search ............................. 445/22; 362/138,
362/139, 216, 252, 800, 33, 227, 249–250,
458, 11; 493/106; 40/582; 355/477

[56] References Cited

U.S. PATENT DOCUMENTS

| | | | |
|---|---|---|---|
| 3,073,210 | 1/1963 | Packard | 40/582 |
| 4,893,223 | 1/1990 | Arnold | 362/252 |
| 5,309,277 | 5/1994 | Deck | 359/387 |
| 5,321,593 | 6/1994 | Moates | 362/251 |
| 5,420,773 | 5/1995 | Huang | 362/410 |
| 5,519,496 | 5/1996 | Borgert et al. | 356/394 |

FOREIGN PATENT DOCUMENTS 4-241476  8/1992  Japan .

*Primary Examiner*—Sandra O'Shea
*Assistant Examiner*—Ismael Negron
*Attorney, Agent, or Firm*—Banner & Witcoff, Ltd.

[57] ABSTRACT

An object of the invention is to make it easy to manufacture the lighting unit 4 in which a plurality of illuminants 1 are arranged on the concave face of a board 2 formed into a shape of a hollow truncated cone. A method of manufacturing a lighting unit comprises the steps of holding a flexible circular printed circuit board 2 having a concentric circular hole and a cutout which has at least two sides 2a, 2b in a planar state, embedding a plurality of illuminants 1 in the board, and jointing one side 2a of the cutout and the other side 2b of the cutout or holding both sides 2a, 2b in close contact so as to place the illuminants 1 in the side of the concave face of the board 2.

1 Claim, 4 Drawing Sheets

METHOD OF MANUFACTURING A LIGHTING UNIT FOR INSPECTING A SURFACE

BACKGROUND OF THE INVENTION

This invention relates to a method of manufacturing a lighting unit which is preferably used when a product inspection is conducted by means of reflected light emitted by the lighting unit.

As a method for examining a surface of a product it has generally been known that a product to be examined is irradiated by a lighting unit through its underside and then the reflected light is visually inspected or taken a photo in close proximate to the lighting unit. If there exists some unevenness in light intensity on the surface to be examined, it may happen that a micro flaw or a finishing defect on the surface of the product to be examined is failed to be detected. Therefore, in order to examine a surface of a product it is very popular to use a lighting unit having such an arrangement that a plurality of illuminants such as light-emitting diodes are placed all over the underside of the lighting unit and the whole underside thereof emits light areally so as to keep the light intensity on the surface to be examined even. Especially in case that a product to be examined is three-dimensional, it is necessary to light up the product to be examined from not only one direction but also several directions as if to cover the product. In such a case it is usual to use a lighting unit having such an arrangement that the underside of the lighting unit, namely the surface which emits light is a concave face of a hollow truncated cone shape and that a plurality of illuminant are arranged on the concave face.

However, if a lighting unit has the above-mentioned arrangement, in order to place a plurality of illuminants all over the underside of the lighting unit, complicated steps have to be taken, such as to process the underside of the lighting unit to form a concave face of a hollow truncated cone or a hollow conic, to perforate a plurality of holes on the concave face, to embed illuminants in each of the holes respectively, and then to wire each of the illuminants by hand. This makes it difficult to assemble the lighting unit having the above-mentioned arrangement, thereby taking longer time to assemble the lighting unit. This also makes it difficult to standardize a process of manufacturing a variety of lighting units having different angle of emitting light because every step such as processing the underside of the lighting unit or the angle of a hole perforated varies.

It is an object of the present invention to provide a method of manufacturing a lighting unit characterized by that the lighting unit having such an arrangement that a plurality of illuminants are set up on a concave face of a hollow truncated cone shape can easily be manufactured.

SUMMARY OF THE INVENTION

In order to accomplish the above-mentioned object the invention has adopted the following method. The method of manufacturing a lighting unit in accordance with the invention comprises the following steps of holding a flexible circular board having a concentric circular hole and a cutout which has at least two sides in a planar state, embedding a plurality of illuminants in the board, and jointing one side of the cutout and the other side of the cutout or holding both sides in close contact so as to place the illuminants in the side of the concave face. With the above-mentioned method, a plurality of illuminants can easily be set up on a concave face of the hollow truncated cone-shaped board.

More specifically, the invention is a method of manufacturing a lighting unit characterized by obtaining the lighting unit in which a plurality of illuminants are arranged on a concave face of a board formed into a shape of a hollow truncated cone and the illuminants are mounted on the underside of the lighting unit through the board by the steps of holding the flexible circular board having a concentric circular hole and a cutout which has at least two sides in a planar state, embedding a plurality of illuminants such as light-emitting diodes or the like in the board, and then jointing one side of the cutout and the other side of the cutout of the board or holding both sides in close contact.

In particular, in order to further simplify assembling operations, it is preferable to use a printed circuit board as the above-mentioned board so that the operations of wiring each illuminants and embedding each illuminants in a board can be done at once.

In accordance with the invention, the following effects are achieved.

It becomes possible to easily set up a plurality of illuminants on a concave face of a hollow truncated cone-shaped board by the following steps. First, hold the flexible circular printed circuit board having a concentric circular hole and a cutout which has at least two sides in a planar state. Next, embed a plurality of illuminants in the board. Finally, joint one side of the cutout and the other side of the cutout or hold both sides in close contact so as to place the illuminants in the side of the concave face. As a result of this, it is not necessary to provide a complicated process to the underside of the lighting unit, which makes it easy to assemble the lighting unit, thereby to shorten the time required to assemble. In addition, since emitting angle can easily be changed just by changing a diameter of a board or a size of a cutout, it is easy to manufacture a variety of lighting units with various angle of emitting light up so as to fit to light a product to be examined.

If a printed circuit board is used as a board, wiring operation is completed just by embedding the illuminants in the board. Then a process of assembling the lighting unit is simplified because a complicated process such as wiring each of the illuminants can be omitted.

BRIEF DESCRIPTION OF THE DRAWINGS

The objects and features of the invention may be understood with reference to the following detailed description of illustrative embodiments of the invention, taken together with the accompanying drawings in which.

DETAILED DESCRIPTION OF THE PREFERRED EMBODIMENTS

An embodiment of the invention will now be described below with reference to FIG. 1 and FIG. 2.

Figure 1:
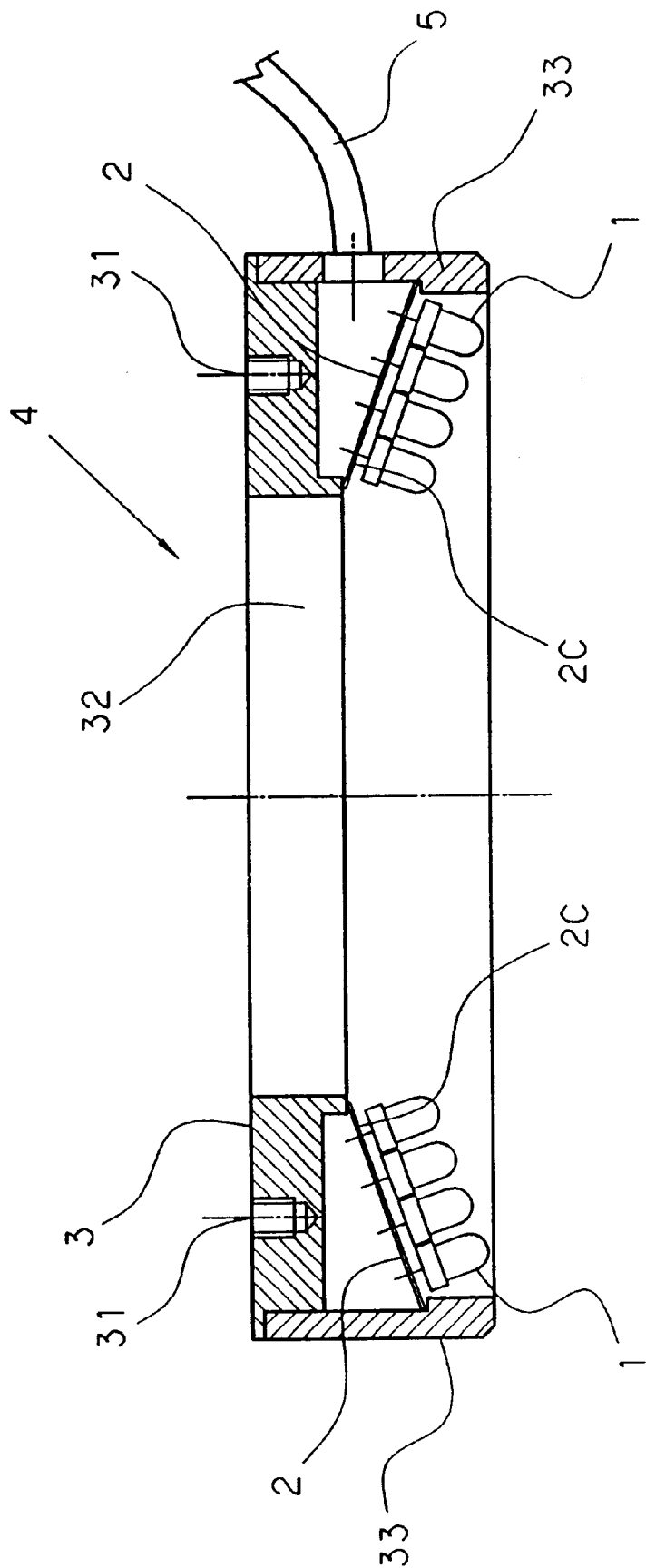
FIG. 1 is a cross sectional end view of a lighting unit showing a preferred embodiment of this invention.
Figure 2:
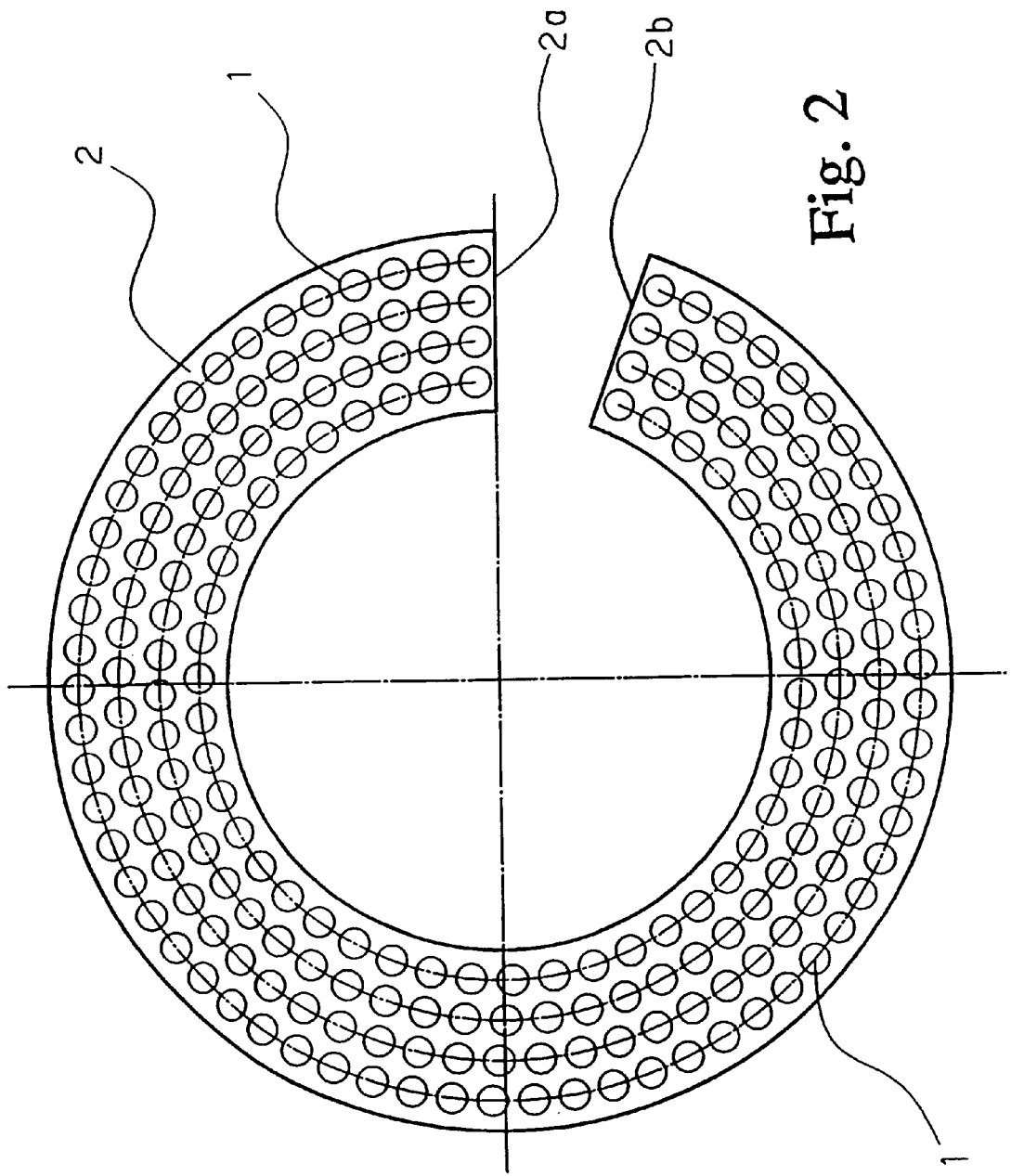
FIG. 2 is a front view showing the board on which illuminants are mounted prior to assembling of the lighting unit shown in FIG. 1.

As shown in FIG. 1, a plurality of illuminants 1 such as light-emitting diodes are arranged on a underside of a lighting unit 4, namely on a concave face 2c of a hollow truncated cone-shaped flexible printed circuit board 2 and a lighting case 3 holds the illuminants 1 together with the board 2. Power is supplied to each of the illuminants 1 from a power cable 5 through the board 2. The lighting case 3 is provided with a center hole 32 for visual inspection or taking photos and a frame 33 for retaining the illuminants 1 and the board 2. An internal thread 31 formed in the lighting case 3 is for mounting the lighting unit 4.

With the above-mentioned arrangement, a method of manufacturing a lighting unit in accordance with the invention will now be explained. First, hold a flexible printed circuit board 2 in a planar state. The shape of the board 2 is a circle with a concentric circle hole and a cutout having two sides 2a, 2b. Next, embed the illuminants 1 in the board 2 by means of soldering or the like. Then joint one side 2a of the cutout and the other side 2b of the cutout or keep both sides 2a, 2b in close contact so as to place the illuminants 1 in the side of a concave face 2c. Then the board 2 is inevitably transformed into a shape of a hollow truncated cone and the illuminants 1 are set up on the concave face 2c of the hollow truncated cone-shaped board 2. At the same time wire a power cable 5 in the board 2 by means of soldering or the like. Finally, mount thus formed board 2 and illuminants 1 to the lighting case 3 through the frame 33, thereby to manufacture the lighting unit 4.

Figure 3:
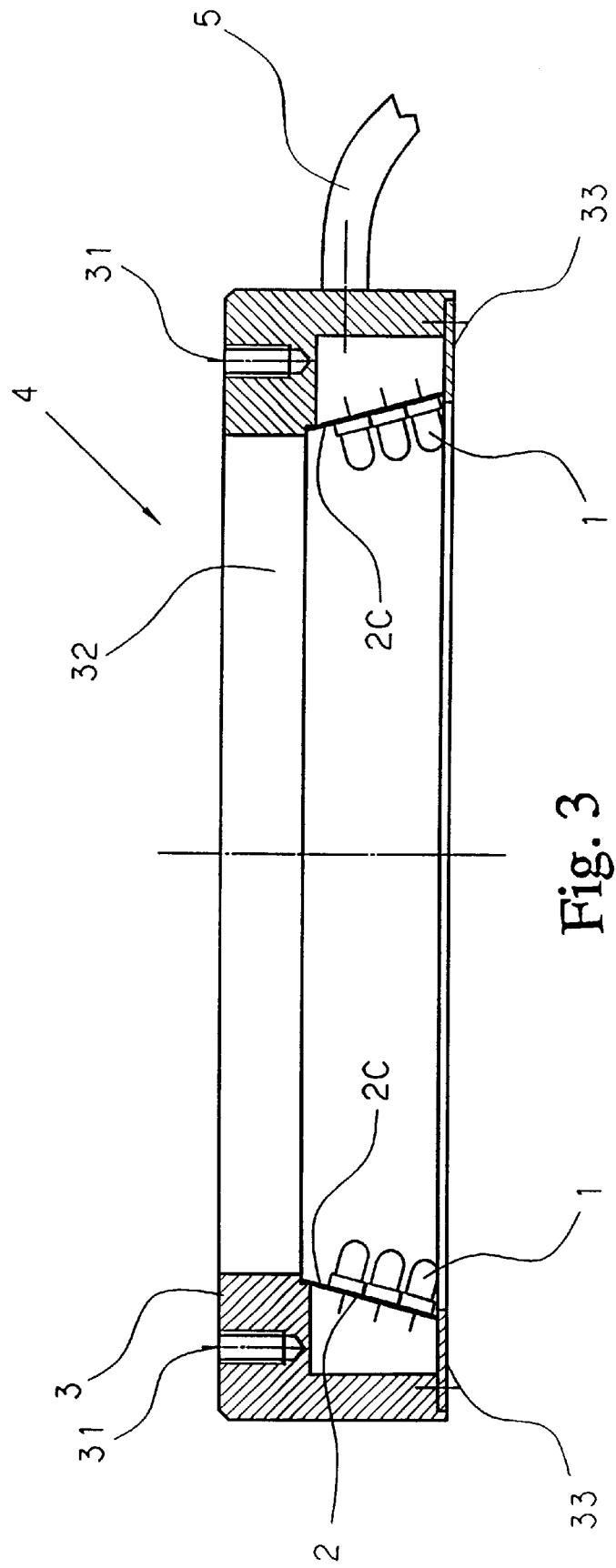
FIG. 3 is a cross sectional end view of a lighting unit showing a modification of the preferred embodiment.
Figure 4:
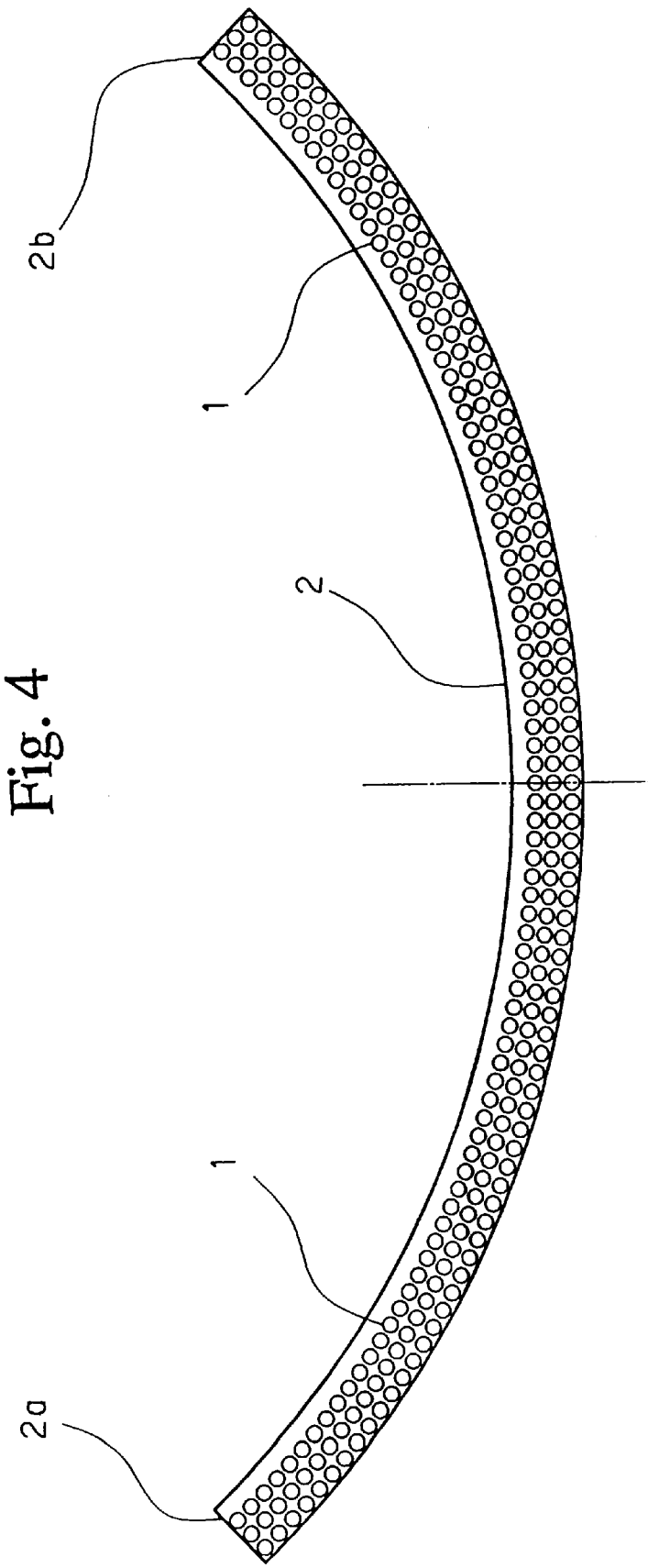
FIG. 4 is a front view showing the board on which illuminants are mounted prior to assembling of the lighting unit shown in FIG. 3.

In accordance with the above-mentioned method of manufacturing the lighting unit 4, it is possible to embed the illuminants 1 in the board 2 when the board 2 is in a planar state. Therefore, in this case the same method can be applied as the method by which electrical parts are mounted on an ordinal printed circuit board. In addition to that, since the printed circuit board 2 is used as a board, wiring operation can be omitted just by embedding the illuminants 1 in the board 2 by means of soldering or the like, thereby to simplify a process of assembling the lighting unit 4. When one side 2a of the cutout and the other side 2b of the cutout are jointed or both sides 2a, 2b are kept in close contact so as to place the illuminants 1 in the side of a concave face, the board 2 is bent and inevitably transformed into a shape of a hollow truncated cone, which makes it easy to arrange the illuminants 1 on the concave face 2c of the hollow truncated cone-shaped board 2. Thus formed board 2 and illuminants 1 are easily mounted to the underside of the lighting case 3 through the frame 33. Also there is no need of processing the lighting case 3 into a shape of concave of a conic or a truncated cone nor need of perforating holes to embed illuminants. As shown in FIGS. 3 and 4, a hollow truncated cone shape having an arbitrary size and angle can easily be formed just by changing a diameter of the board 2 or a size of a cutout. In addition, emitting angle can easily be changed just by changing the frame 33 tailored to fit the truncated cone shape, namely by changing only a part of the lighting unit.

This invention is not limited to the embodiments described in detail hereinabove. For example, the board 2 may be a shape of ellipsoid having a cutout to vary a shape of a surface emitting light.

Moreover, each of the arrangements is not limited to that illustrated in the figures and there may be various modifications without departing from the spirit and essential characteristics thereof.

What is claimed is:

1. A method of manufacturing a lighting unit for inspecting a surface, the lighting unit having an opening at the center thereof for visually inspecting or taking photos of the surface to be inspected, wherein said method comprises the steps of:

holding a flexible circular printed circuit board having a concentric circular hole and a cutout which has at least two sides in a planar state, embedding a plurality of illuminants in said printed circuit board, jointing one side of the cutout and the other side of the cutout of said printed circuit board or holding both sides in close contact so as to form the printed circuit board into a shape of a hollow truncated cone with the illuminants placed in a side of a concave face of said printed circuit board, and positioning a frame about said printed circuit board and retaining said circuit board in said shape of a hollow truncated cone using said frame so as to obtain the lighting unit in which a plurality of illuminants are arranged on the concave face of the printed circuit board formed into the shape of a hollow truncated cone.

\* \* \* \* \*